United States Patent [19]

Brisson et al.

[11] Patent Number: 4,602,171

[45] Date of Patent: Jul. 22, 1986

[54] INHALATION TRANSDUCER CIRCUIT WITH DC DRIFT COMPENSATION

[75] Inventors: Alfred G. Brisson, Schaumburg; Christopher Nowacki, Arlington Heights, both of Ill.

[73] Assignee: Trutek Research, Inc., Arlington Hts., Ill.

[21] Appl. No.: 415,735

[22] Filed: Sep. 7, 1982

[51] Int. Cl.[4] .................... G06G 7/10; H03B 1/00
[52] U.S. Cl. ............................ 307/491; 328/162
[58] Field of Search .......... 330/259, 270, 290, 291; 328/168, 162, 173, 165, 167; 307/490, 491, 494; 128/725

[56] References Cited

U.S. PATENT DOCUMENTS 3,176,236  3/1965  Abbott et al. .................. 330/290
3,419,809  12/1968  Lach et al. ..................... 330/97
3,579,124  5/1971  O'Hara ........................... 307/491
3,737,798  6/1973  Faraguet et al. ................ 330/9

Primary Examiner—Stanley D. Miller
Assistant Examiner—Timothy P. Callahan
Attorney, Agent, or Firm—Trexler, Bushnell & Wolters, Ltd.

[57] ABSTRACT

An inhalation transducer circuit is provided for use with a transducer having a variable electrical output. Early amplifier stages provide very high gain, and are subsequently a.c. coupled to stages of lesser gain leading to a microprocessor and an output. An electronic switch is connected to the a.c. coupling circuit, and when no breathing is being measured and there is no output to the amplification circuit this switch is periodically closed to connect a reference voltage to the a.c. coupling, and thus to compensate for any DC drift in the transducer and early amplification stages.

9 Claims, 2 Drawing Figures

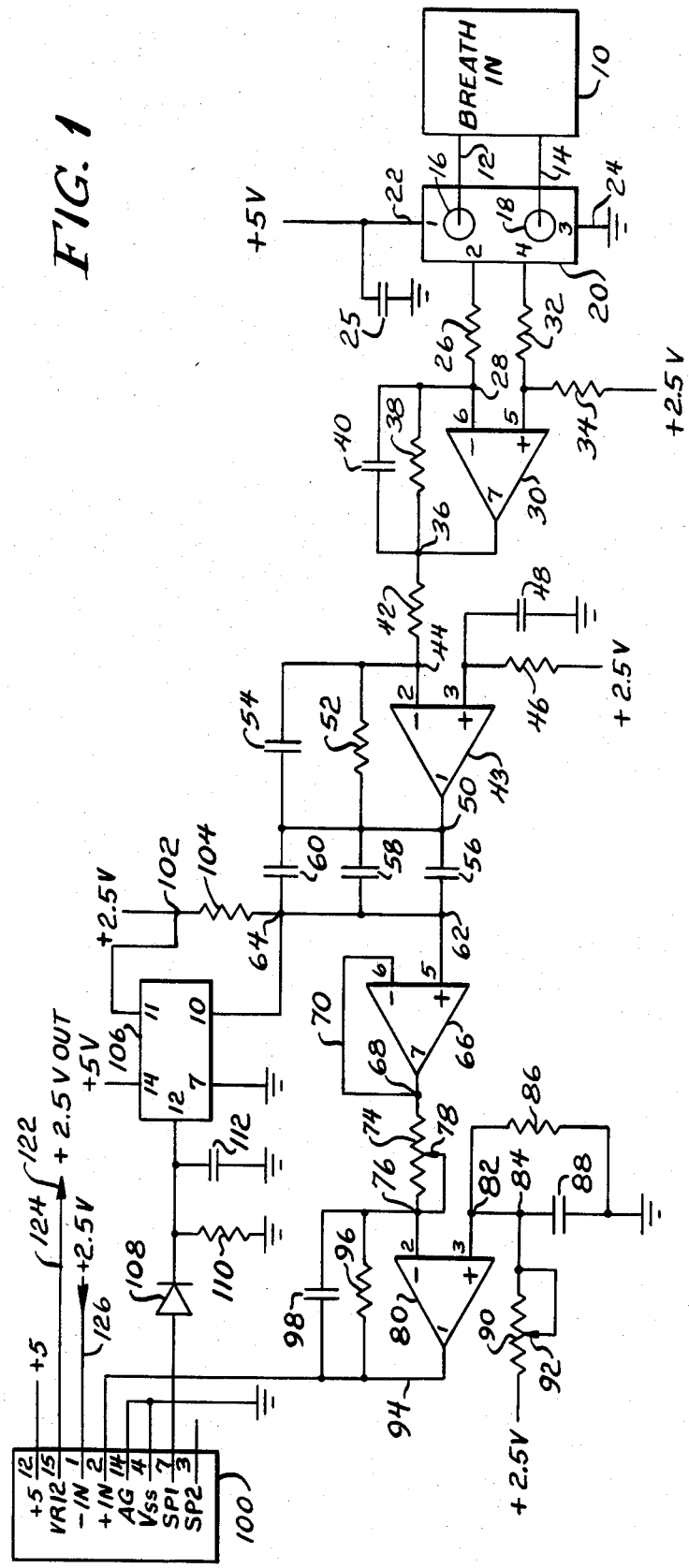
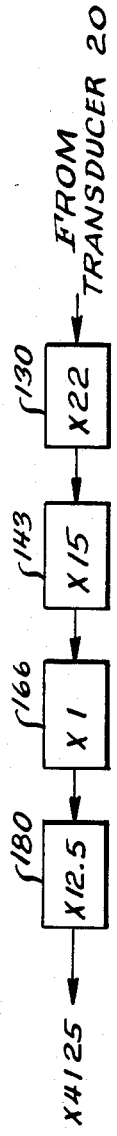
FIG. 1
FIG. 2

INHALATION TRANSDUCER CIRCUIT WITH DC DRIFT COMPENSATION

BACKGROUND OF THE INVENTION

In the testing of lung capacity and the ability of a person to inhale it is known to use an inhalation valve to produce a change or differential in air pressure which is pneumatically connected to a transducer to produce an electric voltage which is a function of the change or differential in air pressure. The change or differential in air pressure produced is not very great, and in the past this has required very sensitive transducers that have been quite expensive. One typical such transducer costs on the order of about $300.

OBJECTS AND SUMMARY OF THE PRESENT INVENTION

A principle object of the present invention is to provide an inhalation transducer circuit for use with a much less expensive transducer than heretofore used in the present art.

It is a related object of the present invention to provide an inhalation transducer circuit utilizing a low output transducer with a very high gain amplifier which is free of drift.

In obtaining the foregoing and other objects of the present invention we utilize an inexpensive transducer costing on the order of $20 to $30 to convert a differential air pressure to an electric voltage of low level. This voltage is amplified quite considerably, with high amounts of gain concentrated in the first stages of amplification, with a.c. coupling to final stages of rather low gain to avoid DC drift. The a.c. coupling includes a time constant circuit having capacitors and a resistor, and a CMOS switch is connected across the resistor. The CMOS switch is closed every three seconds as long as there is no signal from the transducer in order to rezero the voltage on the capacitors. The CMOS switch is disabled when a patient is breathing and his signal is transduced.

THE DRAWINGS

The invention will best be understood when the following specification is read in conjunction with the accompanying drawings wherein:

FIG. 1 is an electronic circuit diagram of the present invention; and

FIG. 2 is a block diagram showing the stages of gain or amplification.

DETAILED DISCLOSURE OF THE ILLUSTRATIVE EMBODIMENT

The circuit as disclosed herein is used in conjunction with an inhalation valve 10 labelled "BREATH IN", and this inhalation valve provides a differential pressure on pneumatic lines 12 and 14. The inhalation valve 10 is preferably that disclosed and claimed in U.S. Pat. No. 4,456,016 issued June 26, 1984 to Nowacki et al.

The pneumatic lines 12 and 14 are connected to pneumatic inputs 16 and 18, respectively, of a transducer 20. The transducer is of a type having a piezo-electric device therein which produces a signal when a positive pressure is applied to one side, or a negative pressure is applied to the other side. In accordance with the present invention a pressure differential is applied across the piezo-electric device, thus enhancing its response. The transducer is provided with a +5 volt potential at 22 connected to pin 1 and is grounded at 24 on pin 3. A capacitor 26 shunts the voltage at 22 to ground to avoid fluctuations in voltage.

The transducer 20 is of a type which can be purchased for $20 to $30, one such transducer being sold by Honeywell under part No. 125PC05D1. This transducer is designed to operate over a range of five pounds per square inch. However, in the present instance a pressure differential of only about 5 centimeters of water is applied, whereby only a small portion of the range of the transducer is used. At its full capacity the transducer will produce an output of 70 millivolts, but due to the small range of the transducer used here only about 400 microvolts is produced from the transducer.

Pin 2 is connected through a resistor 26 to a junction 28 leading to the negative input at pin 6 of an operational amplifier 30. This operational amplifier conveniently is one-half of a package sold by Motorola as MC34002AN. Pin 4 of the transducer 20 is connected through a resistor 32 to the positive input at pin 5 of the operational amplifier 30. And this is connected also through a resistor 34 to a 2.5 volt supply. The output of the operational amplifier 30 is taken from pin 7 and leads to a junction 36. The junction is fed back to junction 28 through the parallel combination of a resistor 38 and capacitor 40.

The junction 36 further is connected through a resistor 42 to the negative input at pin 2 of the second operational amplifier 43 of the package, a junction 44 being included on the connecting line. The positive input at pin 3 is connected through a resistor 46 to a positive 2.5 volt supply, and this is shunted by a capacitor 48 connected to ground.

The output of the second operational amplifier 43 is taken from pin 1 and leads to a junction 50. The junction 50 is connected back to junction 44 through the parallel combination of the resistor 52 and a capacitor 54. The output from the junction 50 is connected through the parallel combination of three capacitors 56, 58, and 60 to junctions 62 and 64.

Junction 62 is connected to positive input pin 5 of operational amplifier 66. This again comprises one-half of a dual operational amplifier package which is conveniently identical with the first one. The output is taken at pin 7 and leads to a junction 68 having a direct feedback line 70 to a negative input pin 6. This connection is to provide unity gain through the operational amplifier 66.

The output junction 68 is connected to a resistor 74 leading to a junction 76. This junction is connected to a sliding tap 78 on the resistor 74 to vary the effective resistance thereof. The junction further is connected to the negative input pin 2 of the second operational amplifier 80 in the package along with the operational amplifier 66. Positive input pin 3 is connected to junction points 82 and 84 which provide a parallel resistor 86 and capacitor 88 in shunt to ground. Junction point 84 also is connected to a resistor 90 leading to the positive 2.5 volt supply. A sliding tap 92 on the resistor 90 is connected back to the line between the resistor and junction point 84 for variation of the resistor to provide an offset adjustment.

The output from the operational amplifier 80 is taken from pin 1 on a line 94, and a parallel resistor 96 and capacitor 98 combination feeds back to the junction 76. The output line continues to pin 2 of a microprocessor board 100. A preferred form of microprocessor in the present invention is sold by Commodore as No. 6508. The programming of the microprocessor does not particularly form a portion of the present invention, except as will be set forth briefly hereinafter.

2.5 volt potential is supplied to a junction 102 connected through a resistor 104 to the junction 64. The 2.5 volt supply and the junction 102 are also connected to pin No. 11 of a large scale integrated circuit quad CMOS analog switch device 106 sold by Motorola as part No. MC14016BCP. Pin 10 of this device is connected to the junction 64. As will be apparent hereinafter during certain times the pins 10 and 11 are internally short circuited whereby to short circuit the resistor 104.

Pin 14 of the device is provided with a positive 5 volts, while pin 7 is connected to ground. An input is provided to pin 12 from pin 7 of the microprocessor 100 through a diode 108 across a shunting resistor 110 and capacitor 112, the resistor and capacitor being connected to ground as shown. An appropriate input to pin 12 as supplied from pin 7 of the microprocessor board causes pins 10 and 11 to short the resistor 104.

The 2.5 volt potential is derived from pin 15 of the microprocessor board 100 along line 124. 2.5 volts out is indicated by the arrow 122 and is connected to all of the previously mentioned locations supplied with +2.5 volts. This voltage is also connected by a line 126 to pin 1 of the microprocessor board 100. Pin 12 of the microprocessor board 100 provides the positive 5 volts, and pins 4 and 14 are grounded. Pin 3 in the present application is not connected.

Reference now should be made to FIG. 2 in which the input from the transducer 20 is shown as applied to a "black box" 130 indicated as supplying a multiplying factor of 22. This is in the stage involving the operational amplifier 30. The amplifier stage involving the operational amplifier 43 is indicated by rectangle 143 as having a multiplication factor of 15. Thus, rather high amplification, a factor of 330 is obtained in the first two stages. The third stage indicated at 166 and involving the operational amplifier 66 has a multiplication factor of only 1, this operational amplifier 66 being used primarily as a buffer. The final stage 180 involving the operational amplifier 80 has a multiplication factor of 12.5, the entire multiplication factor of the several operational amplifiers being 4125.

The operation of the circuit as heretofore described is such that when the person being tested inhales a pneumatic or air pressure differential appears on the two pneumatic lines 12 and 14. The transducer produces output voltage having a maximum DC output of about 400 microvolts. This is ultimately amplified to about 1.8 volts without any drift caused by aging of the transducer or otherwise. As will be apparent, with the overall multiplication factor of 4,125, a drift of only a half a millivolt could result in an output of zero or nearly five volts for the entire circuit.

As has been noted, the gain is concentrated in the first two amplifier stages, and this is followed by a.c. coupling through the capacitors 56, 58 and 60. The operational amplifier 66 serves as a buffer, and although the gain in the stage involving the operational amplifier 80 has been indicated as 12.5, this is adjustable by means of sliding of the tap 78 on the resistor 74. The time constant of the a.c. coupling during breathing, comprising the three capacitors and the resistor 104 is approximately one minute. The output signal from the final operational amplifier 80 is connected to a suitable readout device by the microprocessor, but this does not comprise a part of the present invention.

As long as there is an output signal on the line 94 produced by breathing, the microprocessor does not provide an output from pin 7. However, when there is not breathing, approximately every three seconds there is a short burst of pulses applied from pin 7 through the diode 108, and this burst of pulses is integrated by the integrator circuit comprising the resistor 110 and capacitor 112 to provide an input to pin 12 of the integrated circuit 108, and this causes an internal direct connection or short circuit between pins 10 and 11, thereby shorting out resistor 104, and bringing the output side of the capacitors on junctions 62 and 64 to the +2.5 reference voltage. The switch closure is only on the order of 10 to 20 milliseconds. It thus will be seen that any tendency for DC drift of the circuit to the right of the capacitors 56, 58 and 60 is fully compensated by the periodic application of 2.5 volts to the output sides of the capacitors.

It will be apparent that there could be a single capacitor rather than the three shown, but the three are used in parallel in order to obtain the desired capacity at a reasonable price.

Although appropriate circuit values will no doubt occur to those skilled in the art, representative values which have been found to work are set forth hereinafter by way of example:

Resistor 26=10K OHMS
Resistor 32=10K OHMS
Resistor 34=220K OHMS
Resistor 38=220K OHMS
Resistor 42=10K OHMS
Resistor 46=10K OHMS
Resistor 52=150K OHMS
Resistor 74=20K OHMS
Resistor 86=2.2M OHMS
Resistor 90=20K OHMS
Resistor 96=150K OHMS
Resistor 104=20M OHMS
Resistor 110=180K OHMS
Capacitor 25=0.1 uF
Capacitor 40=0.10 uF
Capacitor 48=2.2 uF
Capacitor 54=0.1 uF
Capacitor 56=1 uF
Capacitor 58=1 uF
Capacitor 60=1 uF
Capacitor 88=2.2 uF
Capacitor 98=0.1 uF
Capacitor 112=0.01 uF The specific example of the invention as herein shown and described is for illustrative purposes. Various changes in structure will no doubt occur to those skilled in the art and will be understood as forming a part of the present invention insofar as they fall within the spirit and scope of the appended claims.

The invention is claimed as follows:

1. An inhalation transducer circuit comprising an air pressure-to-electric potential transducer for producing an electric potential proportional to a person's air inhalation capacity, said electric potential so produced being of a low magnitude, first electronic amplification means for receiving and amplifying said potential, second electronic amplification means for further amplifying said potential, a.c. coupling means between said first and said second amplification means, output means connected to said second amplification means and providing an output signal which is a greatly amplified function of said electric potential, said output means having an output potential only when said transducer has a potential, means providing a predetermined reference potential, restoring means connected to said a.c. coupling means and to said reference potential providing means and selectively conductive for periodically restoring said a.c. coupling means to said predetermined reference potential to avoid drift originating in said transducer or in said first amplification means, and said output means being connected to said restoring means and operating said restoring means only in the absence of said output potential.

2. A transducer circuit as set forth in claim 1 wherein said first electronic amplification means has an output terminal and said second electronic amplification means has an input terminal, said a.c. coupling means comprises capacitor means connected in series between said first electronic amplification means output terminal and said second electronic amplification means input terminal, and resistor means being connected from said input terminal to said reference potential providing means, said restoring means comprising means for periodically connecting said reference potential providing means directly to said input terminal bypassing said resistor means.

3. A transducer circuit as set forth in claim 2 wherein said restoring means comprises switch means parallel to said resistor and periodically closed to short said resistor.

4. A transducer circuit as set forth in claim 3 wherein said switch means comprises electronic switch means.

5. As transducer circuit as set forth in claim 4 wherein said restoring means further includes means interconnecting said output means and said electronic switch means said output means periodically closing said electronic switch means in the absence of an output signal.

6. A transducer circuit as set forth in claim 5 wherein said output means provides a series of short bursts of pulses to said interconnecting means in the absence of an output signal.

7. A transducer circuit as set forth in claim 6 wherein said interconnecting means comprises integrating means for integrating each burst of pulses.

8. A transducer circuit as set forth in claim 1 wherein said restoring means comprises an electronic switch connected between said a.c. coupling means and said reference potential providing means for periodically connecting said reference potential to said a.c. coupling means.

9. A transducer circuit as set forth in claim 1 wherein said first electronic amplification means has a much higher gain than said second amplification means by a factor of substantially at least 10.

* * * * *